(12) United States Patent
Tappehorn et al.

(10) Patent No.: US 11,504,493 B2
(45) Date of Patent: Nov. 22, 2022

(54) CURVED CONNECTION UNIT FOR CONNECTING A PATIENT TO A MEDICAL DEVICE

(71) Applicant: Drägerwerk AG & Co. KGaA, Lübeck (DE)

(72) Inventors: Ludger Tappehorn, Lübeck (DE); Matthias Hoder, Lübeck (DE); Jan-Henning Lütkhoff, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 114 days.

(21) Appl. No.: 17/159,958

(22) Filed: Jan. 27, 2021

(65) Prior Publication Data
US 2021/0228831 A1 Jul. 29, 2021

(30) Foreign Application Priority Data
Jan. 28, 2020 (DE) ...................... 10 2020 000 503.9

(51) Int. Cl.
*A61M 16/08* (2006.01)

(52) U.S. Cl.
CPC ..... *A61M 16/0816* (2013.01); *A61M 16/0833* (2014.02); *A61M 2207/00* (2013.01)

(58) Field of Classification Search
CPC .......... A61M 16/0816; A61M 16/0833; A61M 16/0841; A61M 39/10; A61M 2039/1072; A61M 2039/1077; A61M 2207/00
See application file for complete search history.

(56) References Cited

U.S. PATENT DOCUMENTS

| 5,156,159 | A | 10/1992 | Lampotang et al. |
| 5,694,922 | A | 12/1997 | Palmer |
| 6,193,697 | B1 * | 2/2001 | Jepson ............... A61M 5/162 604/905 |
| 9,295,805 | B2 | 3/2016 | Worboys et al. |
| 10,898,667 | B2 | 1/2021 | Millar et al. |
| 2004/0221852 | A1 | 11/2004 | Madsen |
| 2010/0147296 | A1 | 6/2010 | Brewer et al. |
| 2011/0067699 | A1 | 3/2011 | Caruso et al. |

(Continued)

FOREIGN PATENT DOCUMENTS

| DE | 102008022987 A1 | 11/2009 |
| DE | 102016119707 A1 | 4/2018 |

(Continued)

*Primary Examiner* — Matthew P Travers
(74) *Attorney, Agent, or Firm* — McGlew and Tuttle, P.C.

(57) ABSTRACT

A connection unit establishes a fluid connection between a patient and a ventilator. The connection unit includes a patient-side connection piece, a device-side connection piece, a port piece and a central piece, which provides a tube with a curved tube segment and is connected with a fluid-tight connection to the two connection pieces. The port piece includes a straight tube segment and a bent surface with a bent surface and with a passage opening. The port piece is inserted into a receiving opening of the central piece. The bent surface of the port piece forms a part of a wall of the curved tube segment. The straight tube segment of the port piece and the central piece provide a straight tube, which is interrupted by the passage opening. An additional device is insertable through the straight tube segment and through the passage opening into the provided tube.

21 Claims, 8 Drawing Sheets

(56) References Cited

U.S. PATENT DOCUMENTS

| | | |
|---|---|---|
| 2013/0296653 A1 | 11/2013 | Brown et al. |
| 2016/0051792 A1 | 2/2016 | Hallett et al. |
| 2016/0310688 A1 | 10/2016 | Rothermel |
| 2017/0258550 A1 | 9/2017 | Vazales |
| 2019/0167937 A1 * | 6/2019 | Sims ................. A61M 16/0688 |
| 2019/0240435 A1 | 8/2019 | Anderson et al. |

FOREIGN PATENT DOCUMENTS

| | | | |
|---|---|---|---|
| WO | 9626757 A1 | 9/1996 | |
| WO | WO-2011142678 A1 * | 11/2011 | ........ A61M 16/0816 |
| WO | 2014205513 A1 | 12/2014 | |
| WO | 2018236228 A1 | 12/2018 | |

* cited by examiner

CURVED CONNECTION UNIT FOR CONNECTING A PATIENT TO A MEDICAL DEVICE

CROSS REFERENCE TO RELATED APPLICATIONS

This application claims the benefit of priority under 35 U.S.C. § 119 of German Application 10 2020 000 503.9, filed Jan. 28, 2020, the entire contents of which are incorporated herein by reference.

TECHNICAL FIELD

The present invention pertains to a connection unit, by means of which a patient can be connected to a medical device, especially to a ventilator, wherein the connection unit changes the flow direction of a fluid and makes it possible to insert an intracorporeal device. The present invention pertains, furthermore, to a use of such a connection unit as well as to a process for manufacturing such a connection unit.

TECHNICAL BACKGROUND

Various such connection units have become known.

U.S. Pat. No. 5,694,922 describes a connection unit (adaptor), which is capable of connecting a patient to flexible tubing (exterior tubing). The L-shaped connection unit 44 has an opening, through which an additional device can be inserted.

US 2004/0 221 852 A1 shows a ventilator (respiratory apparatus 10) with a catheter (suction catheter 12), which can be inserted into the airways of a patient 18 in order to aspirate secretions. The catheter 12 can be inserted by means of an instrument introduction section 22 with a passageway 24.

How a catheter (suction catheter 12) of a catheter aspirating device 10 is inserted into the airways of a patient is also described in US 2010/0 147 296 A1. The catheter aspirating device 10 can be connected to a multiple-access manifold 20, through which the catheter 12 can be inserted. A port 30 of the manifold 20 can be connected to a port seal cartridge 40.

US 2013/0 296 653 A1 shows a system 100 for mechanical ventilation with a breathing mask 102, which can be placed on the head of a patient, as well as with an adapter 110, which can be coupled with the breathing mask 102. A bent assisted respiration source assembly 119 with a diverter 114 can be inserted into an insertion assembly 117 of the adapter 110. The insertion assembly 117 is connected detachably to a connection assembly 130 of the adapter 110. A valve 128, for example, a nonreturn valve (one-way valve) is installed in the assisted respiration source assembly 119.

SUMMARY

A basic object of the present invention is to provide a connection unit for establishing a fluid connection between a patient and a medical device, wherein the connection unit makes it possible to connect an additional device, and wherein the risk that an undesired situation develops, especially that the patient is put at risk during the connection of the additional device, shall be lower than in prior-art connection units.

The connection unit according to the present invention contributes to the establishment of a fluid connection between a patient-side coupling unit and hence a patient, on the one hand, and a medical device, especially a ventilator, on the other hand. An anesthesia device is a special case of a ventilator. Thanks to this fluid connection, a fluid can flow from the medical device to the patient-side coupling unit and hence to the patient and/or in the opposite direction. A "patient-side coupling unit" can be connected detachably to a patient, for example, be placed on the face or inserted into the body, especially into the trachea or into the esophagus. Special examples of a patient-side coupling unit are a breathing mask, an endotracheal tube and a measuring tube with a measuring balloon.

The patient-side coupling unit is connected to a patient-side fluid guiding unit or can be connected to a patient-side fluid guiding unit. The medical device is connected to a device-side fluid guiding unit or can be connected to a device-side fluid guiding unit.

The connection unit comprises:
- a hollow patient-side connection piece,
- a device-side connection piece,
- a hollow port piece, and
- a hollow central piece.

The port piece comprises
- a straight tube segment and
- a bent surface element with a bent surface, advantageously a thin element.

The term "thin element" designates an element that extends in a—usually bent—surface and has a thickness that is at most half, preferably at most one fourth and especially preferably at most one tenth of the maximum extension of the thin element in the surface. The thin element may comprise a laminar element, a membrane element, a thin plate or other thin wall portion having a curved or bent surface.

The bent surface element has a passage opening. This passage opening is recessed into the bent surface of the bent surface element. The passage opening occupies at most half of the area of the bent surface, preferably at most 20%, especially preferably at most 10% or at most 5%. The passage opening occupies at least 20% of the area of the bent surface.

The central piece comprises a curved tube segment with a wall.

The patient-side fluid guiding unit can be connected or is connected to the patient-side connection piece of the connection unit. A fluid connection can be established by means of this patient-side fluid guiding unit between the connection unit and the patient-side coupling unit. As a result, a fluid connection can or is also established between the connection unit and a patient, who shall undergo medical treatment, for example, shall be ventilated mechanically.

The term "fluid guiding unit" designates a component that can guide fluid from a point along a path to another point without the fluid being able to escape on the side. The term "fluid guiding unit" comprises, in particular, a flexible tubing, e.g., a folded tube, a tube, e.g., a tubular connection element or a connector, as well as a tube or catheter, especially a tube that can be inserted into the trachea or into the esophagus of a patient. The term "tube" designates a fluid guiding unit made of a relatively rigid material, and the term "flexible tubing" is a fluid guiding unit consisting of a flexible material.

A device-side fluid guiding unit can be connected or is connected to the device-side connection piece of the connection unit. A fluid connection can be established or is established by means of this device-side fluid guiding unit between the connection unit and a medical device, especially a ventilator, which shall mechanically ventilate the patient.

The central piece comprises two ends, between which the curved tube segment is located. One end of the central piece is connected in a fluid-tight manner or can be connected in a fluid-tight manner (fluid-tight connected) to the patient-side connection piece. The other end of the central piece is connected in a fluid-tight manner to the device-side connection piece or can be connected in a fluid-tight manner.

The connection unit provides a curved tube, which comprises the two hollow connection pieces and the curved tube segment. This curved tube changes the direction in which a fluid flows through the connection unit.

A fluid can flow through a connected fluid guiding unit, the provided curved tube and the other connected fluid guiding unit from the medical device to the patient-side coupling unit and/or from the patient-side coupling unit to the medical device. The flow direction of the fluid is changed in the curved tube segment, i.e., the fluid is deflected.

The central piece has a receiving opening. The port piece is inserted into this receiving opening or can be inserted into this. When the port piece is inserted, the bent surface of the port piece forms a part of the wall of the curved tube segment of the central piece.

The port piece comprises a straight tube segment. This straight tube segment and the central piece together provide a straight tube. This straight tube is interrupted by the bent surface element of the inserted port piece. The straight tube passes through the passage opening in the bent surface element and continues in the interior of the patient-side connection piece.

The connection unit according to the present invention makes possible the following use thanks to the straight tube: An additional device can be inserted into the interior of the straight tube, which provides the straight tube segment and the central piece. In order to insert the additional device, the additional device can be inserted through the straight tube segment and through the passage opening into the interior of the patient-side connection piece and be moved to the patient-side coupling unit. Since a straight tube is provided, the additional device can have the shape of a rigid rod or of a rigid tube. The risk that the additional device is caught at a wall of a component of the fluid connection or it damages the additional device or the wall is reduced.

According to the present invention, the central piece comprises a curved tube segment, which belongs to the curved tube provided or forms the curved tube. This curved tube segment has a bent surface, preferably without edges and corners. Due to this feature of the bent surface, the curved tube causes a lower flow resistance or a flow resistance varying to a lesser extent with the location than do other connection units when a fluid flows from the medical device through the curved tube to the patient or vice versa, especially when the bent surface is smooth. The risk of development of swirls in the curved tube is lower compared to a configuration in which an edge is formed on the inner wall of the tube. Such swirling may distort the measurement results of a sensor for a parameter of a fluid stream.

These two effects, namely, the lower and/or less markedly varying flow resistance as well as reduced swirling, make it easier to regulate the pressure and/or the volume flow in a fluid connection between the medical device and the patient and to preset a desired time curve of the pressure as a command variable for this regulation. This does, in turn, make it easier, in particular, to reduce the mechanical ventilation of a patient gradually and thereby to "wean" the patient off the mechanical ventilation. If the ventilator is configured as an anesthesia device, this configuration makes it easier to dispense the anesthetic being used correctly.

An additional device can be inserted according to the present invention into the interior of the tube through the port piece. This additional device is, for example, a catheter, with which secretion is aspirated from the patient endotracheally, or a probe or an endoscope.

The straight tube segment of the port piece and the central piece provide according to the present invention a straight tube. The additional device can be inserted through this straight tube. Thanks to the port piece of the connection unit according to the present invention, it is not necessary to sever the fluid connection between the medical device and the patient-side coupling unit in order to insert the additional device. Such a severing would frequently jeopardize the goal of the medical treatment, e.g., it would jeopardize the mechanical ventilation, and re-establishment of the fluid connection takes time. In addition, a closing unit would have to be placed at the severing point, which may lead to contamination. The present invention consequently saves time during the insertion of the additional device and it reduces the risk of contamination.

To insert the additional device, an optional cap or another closure is removed from the straight tube segment of the port piece, and the additional device is moved through the tube segment of the port piece. The closure can be reattached when the additional device has been removed again and the fluid connection is maintained.

A passage opening is recessed according to the present invention into the bent surface element and hence into the bent surface of the port piece. This passage opening occupies at most half, preferably a smaller part, especially at most one fourth, of the area of the bent surface, but not the entire bent surface. The passage opening preferably occupies at least one fifth of the area of the bent surface. As a result, the pressure loss, which develops or may develop during the insertion of the additional device, is lower than if the passage opening occupied a larger part of the bent surface or even the entire width of the port piece. On the other hand, the passage opening is preferably large enough. Since the pressure loss occurring during the insertion of the additional device is lower, the risk of air escaping from the lungs of the patient in an undesired manner and of the lung collapsing as a result is reduced, in particular.

In one embodiment, the port piece is connected rigidly to the central piece, for example, by a welded connection or by a bonded connection or by a suitable positive-locking connection. In another embodiment, the port piece can be inserted detachably into the central piece and can again be removed from the central piece. It is possible that different port pieces, also such having different geometries and/or different dimensions and/or such made of different materials, can be inserted into the central piece one after another and removed again. It is sufficient in many cases to insert a fitting port piece in order to insert an additional device. It is not necessary to use different connection units.

The port piece can be inserted according to the present invention into the central piece. In one embodiment, the port piece snaps in when it reaches, during the insertion, a position in which the bent surface closes flush with the inner wall of the bent tube segment of the central piece. The snapping in is ensured, for example, by a circumferential projection at the port piece or at the central piece. This configuration makes it possible for a gap to develop between the port piece and the central piece, which facilitates the insertion of the port piece. Nevertheless, the port piece is connected to the central piece in a fluid-tight manner after the insertion. It is possible that the port piece is connected permanently to the central piece after the snapping in. It is also possible that the snapped-in port piece can again be pulled out of the central piece.

It is also possible that a snap holder or a bead holds the port piece in the central piece.

In one embodiment, the port piece is manufactured from a port piece material. The central piece and the other components of the connection unit according to the present invention are manufactured from at least one other material. The port piece material preferably has a higher elasticity than the material or each material of the central piece, preferably than the material or each material of the connection unit except for the port piece. This embodiment with the preferably flexible port piece makes it easier to insert the port piece into the receiving opening of the central piece, doing so such that the port piece fills the receiving opening in a fluid-tight manner. Thanks to the higher elasticity, no joining process is needed, aside from the insertion of the port piece, to connect the port piece to the central piece in a fluid-tight manner. In particular, no connection in substance is necessary in many cases.

The connection unit preferably comprises a cap. The straight tube segment of the port piece can be closed reversibly by means of this cap, i.e., the cap can be removed again. Thanks to this cap, the straight tube segment is closed against the environment and is hence protected against the undesired entry of a fluid or of particles as long as no additional device has been inserted. The cap needs only be removed for the purpose of inserting the additional device, and it prevents the entry of a large quantity of fluid from a ventilation circuit. The cap can be reattached after the additional device has been removed again.

In one embodiment, the passage opening is closed by a flexible element. This flexible element is opened when the additional device is inserted. In particular, the cap does not necessarily have to close the straight tube segment in a fluid-tight manner in this embodiment.

The cap is held especially preferably by a suitable holder at the port piece or at another component of the connection unit according to the present invention. This prevents the cap from being lost.

The straight tube segment and the central piece provide according to the present invention a straight tube, through which the additional device can be inserted. This straight tube preferably continues in the patient-side connection piece and in a connected patient-side fluid guiding unit in a straight form, i.e., without a change in direction. Thanks to this configuration, the additional device may comprise a rigid rod-shaped component, which can be displaced through the patient-side fluid guiding unit without jamming The risk of the additional device jamming or of a wall of a component being damaged from the inside or being damaged itself is reduced.

In order to insert an additional device, the additional device must be moved through the bent surface element with the bent surface of the port piece. To make this possible, the bent surface element has a passage opening. In a preferred embodiment, this passage opening is defined at least partially by two mutually opposite sealing lips. In another embodiment, the passage opening is provided by a circumferential sealing lip. The sealing lip or each sealing lip can be pushed aside during the insertion of the additional device, so that the passage opening is enlarged. A sufficiently rigid additional device pushes the sealing lip aside by itself during the insertion. As long as no additional device has been inserted, the passage opening has a smaller cross-sectional area compared to the state in which an additional device has been inserted. This reduces the quantity of fluid that escapes through the passage opening compared to a rigid edge around the passage opening. The passage opening may be made larger without an increased loss due to leakage occurring with the device inserted. The sealing lip or each sealing lip is preferably manufactured from an elastic material.

The connection unit provides according to the present invention a curved tube. This curved tube changes the flow direction of a fluid, which is flowing through the connection unit. The angle by which the flow direction is changed is preferably between 35° and 90°, especially preferably between 50° and 80° and especially between 60° and 70°.

In one embodiment, the curvature of the curved tube provided is brought about only by the curved tube segment. The two hollow connection pieces provide two straight tubes in this embodiment.

The curved tube segment of the central piece belongs to the curved tube provided and has a wall. This wall preferably comprises a bent inner wall segment and a bent outer wall segment. The terms "inside" and "outside" refer to the direction of curvature of the curved tube segment. The two wall segments may be connected to one another rigidly and may have especially a one-piece configuration. The bent surface of the port piece preferably forms a part of the outer wall segment or the entire outer wall segment. The passage opening is consequently recessed into the outer wall segment. Viewed in the flow direction, the bent surface may occupy the entire length of the outer wall segment.

The two embodiments with sealing lips and with the cap may be combined. Thanks to the sealing lips, it is not necessary for the cap to close the port piece in a fully fluid-tight manner, not even in case of an overpressure within the connection unit. It is sufficient that the attached cap reduces the volume flow sufficiently compared to a situation in which the cap is not attached.

The port piece is inserted or can be inserted according to the present invention into the central piece such that the bent surface of the port piece forms a part of the wall of the bent tube segment. This embodiment facilitates in many cases the manufacture of the connection unit according to the present invention with the bent tube segment. It is possible to manufacture the port piece and the other components of the connection unit separately from one another, in which case the central piece has a sufficiently large opening between the two connection pieces. The port piece is later inserted into this receiving opening.

The central piece preferably comprises a connector. This connector encloses the receiving opening of the central piece. The port piece can be inserted into the connector or is inserted into the connector. The embodiment with the connector makes it easier to insert the port piece into the central piece. If a robot is used to manufacture of the connection unit according to the present invention, this connector is capable of guiding a gripping arm or the like of this robot.

According to the present invention, the connection unit comprises a central piece and two connection pieces. The central piece is arranged between the two connection pieces. The two ends of the central piece are connected to a respective connection piece. The central piece is preferably connected rotatably to each connection piece, namely, rotatably about a rotation axis, which extends parallel to the central axis of the respective connection piece. The two rotation axes are at right angles or in an oblique position orientation in relation to one another.

This rotatable configuration reduces the mechanical stress, to which a fluid guiding system of a fluid connection between the medical device and the patient-side coupling unit is subjected, wherein this fluid guiding system comprises the connection unit according to the present invention, a patient-side fluid guiding unit connected to the patient-side connection piece and a device-side fluid guiding unit connected to the device-side connection piece. At least two rotatable connections with different rotation axes make it easier for the fluid guiding system to align itself all by itself such that the lowest possible mechanical stress will occur. This reduces the risk of the fluid connection being interrupted by a kink, which may compromise the flow of fluid, or of the occurrence of damage, especially of a leak.

The present invention pertains, furthermore, to a fluid guiding component, which comprises
- a fluid guiding system comprising a device-side fluid guiding unit and
- a connection unit according to the present invention.

The device-side connection piece of the connection unit is connected or can be connected in a fluid-tight manner to the device-side fluid guiding unit.

The present invention pertains, furthermore, to a fluid guiding device, which comprises a fluid guiding component and a patient-side fluid guiding unit. The fluid guiding component is configured as was just described. The patient-side connection piece of the connection unit is connected or can be connected in a fluid-tight manner to the patient-side fluid guiding unit. A patient-side fluid guiding unit is connected or can be connected in a fluid-tight manner to a patient-side coupling unit.

Furthermore, the present invention pertains to a fluid guiding system. This fluid guiding system comprises a fluid guiding device, which is configured as was just described, and a patient-side coupling unit. The patient-side fluid guiding unit is connected or can be connected in a fluid-tight manner to a patient-side coupling unit.

The present invention pertains, furthermore, to a medical system, which is configured for a medical treatment of a patient. This medical system comprises
- a medical device, especially a ventilator, which may be configured as an anesthesia device,
- a device-side fluid guiding unit,
- a patient-side fluid guiding unit,
- a patient-side coupling unit, which can be connected detachably to a patient, can be placed, in particular, on the face or can be inserted into the body of the patient, and
- a connection unit according to the present invention.

The medical device is connected or can be connected in a fluid-tight manner to the device-side fluid guiding unit. The device-side fluid guiding unit is connected or can be connected in a fluid-tight manner to the device-side connection piece of the connection unit. The patient-side connection piece of the connection unit is connected or can be connected in a fluid-tight manner to the patient-side fluid guiding unit. The patient-side fluid guiding unit is connected or can be connected in a fluid-tight manner to the patient-side coupling unit.

A preferred process of manufacturing a connection unit according to the present invention comprises the following steps:
- The port piece is manufactured.
- The two connection pieces are manufactured.
- The central piece is manufactured, namely, such that the receiving opening is formed in the wall of the central piece.
- The port piece is inserted into the receiving opening. The insertion is carried out such that the bent surface of the port piece closes the receiving opening.
- The central piece is connected to the two connection pieces in a fluid-tight manner.

This manufacturing process makes it possible to manufacture the port piece separately from the other components of the connection unit. It is possible in many cases to manufacture each component of the connection unit without undercuts.

It is possible to manufacture a set of similar patient-side connection pieces, device-side connection pieces and central pieces as well as at least two sets of two different port pieces, wherein these port pieces differ in their geometry and/or in at least one dimension. Both different port pieces can be inserted into the central piece, optionally into the one port piece or into the other. This configuration makes it easier to manufacture connection units for different insertable additional devices and to nevertheless utilize the advantages of a manufacture in large quantities. The connection pieces and central pieces can be manufactured in a larger quantity, and the sets of port pieces in respective smaller quantities.

In a preferred embodiment, the port piece is inserted at first into the central piece. The two connection pieces are then connected to the central piece in a fluid-tight manner. This embodiment makes it easier to provide an optional strap for an optional cap. In another embodiment, the two connection pieces are connected at first to the central piece to form a component, and the port piece is then inserted. It is also possible to manufacture the two connection pieces as one component and to insert the port piece into this one component.

The two connection pieces and the central piece are preferably manufactured from the same material. The two connection pieces and the central piece are preferably manufactured by an injection molding process.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF PREFERRED EMBODIMENTS

Figure 1:
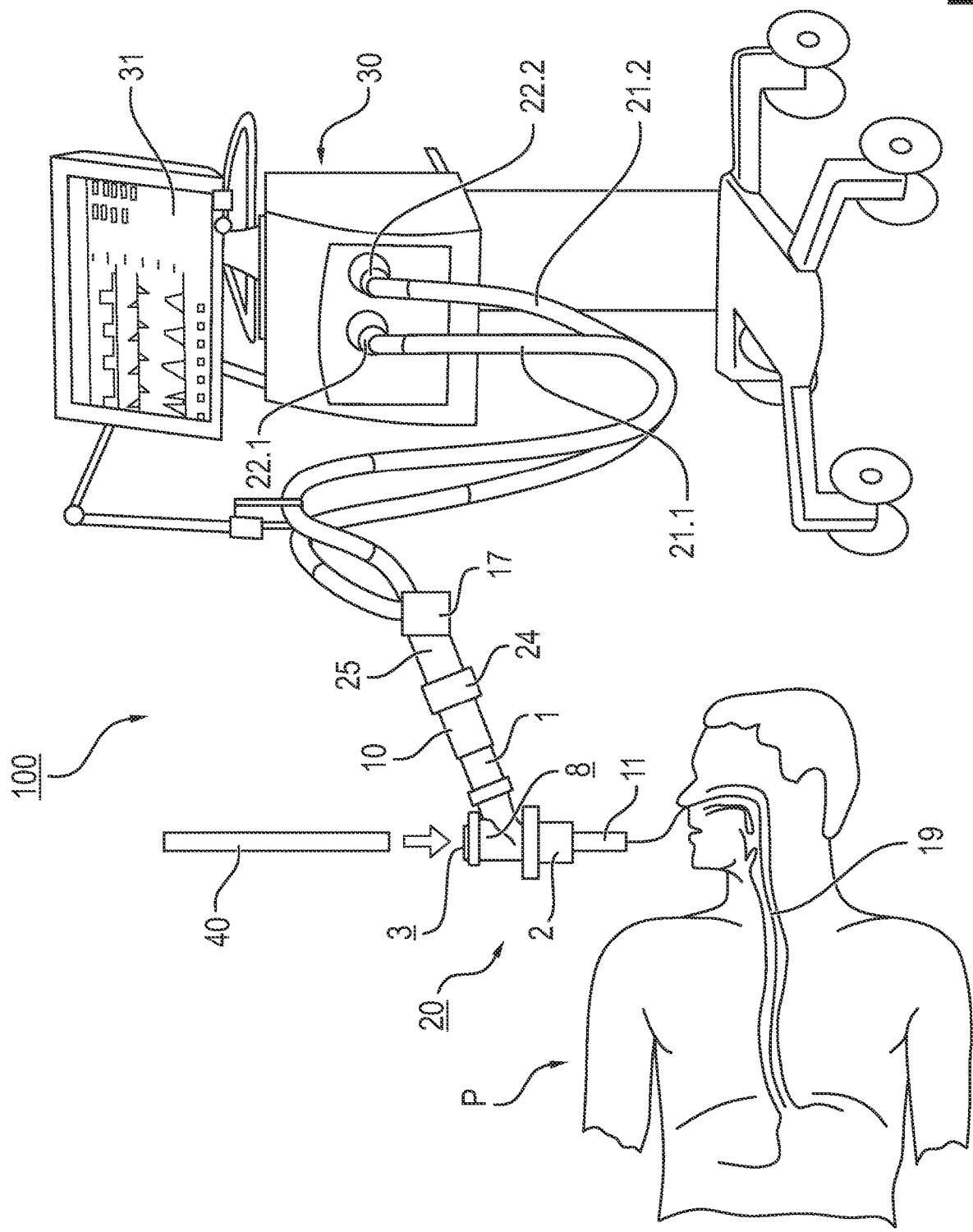
FIG. 1 is a schematic view showing a ventilator, which is connected by a fluid guiding system to a patient-side coupling unit in the body of a patient to be ventilated.

Referring to the drawings, FIG. 1 shows a ventilator 30, which is capable of mechanically ventilating a patient P.

This ventilator 30 may also be configured as an anesthesia device, which feeds at least one anesthetic to the patient. FIG. 1 shows, furthermore, the mechanically ventilated patient P.

The time curves of different vital parameters of the patient P are displayed on a display device 31 of the ventilator 30. The ventilator 30 is in a fluid-tight fluid connection with the patient P, so that fluid can flow from the ventilator 30 to the patient P, and a ventilation circuit, in which fluid can flow both from the ventilator 30 to the patient P and also in the opposite direction, from the patient P to the ventilator 30, is optionally formed. This fluid connection is formed by a fluid guiding system 100, which comprises the following components in the exemplary embodiment being shown:
- a patient-side coupling unit 19 in the form of a measuring tube, which is inserted into the esophagus of the patient P and extends, for example, into the stomach, or in the form of a ventilating tube, which is inserted into the trachea of the patient P and extends into the lungs,
- a patient-side fluid guiding unit in the form of a connector 11, which is tubular in the exemplary being shown and which is connected in a fluid-tight manner to the patient-side coupling unit 19,
- a tubular connector 10, which belongs to a device-side fluid guiding unit,
- two parallel flexible tubing 21.1, 21.2 for the inhalation and for the exhalation, respectively,
- two connection elements 22.1 and 22.2, which connect the two device-side flexible tubing 21.1 and 21.2 rotatably to the ventilator 30,
- a Y-piece 17, which connects the two flexible tubing 21.1 and 21.2 to the connector 10,
- a filter unit, and
- a connection unit 20 according to the present invention.

The filter unit comprises a filter element 24 as well as two fluid guiding units 10, 25 in the form of two tubular connectors, between which the filter element 24 is located. The connection unit 20 according to the present invention is connected to both connectors 10 and 11 in a fluid-tight manner and rotatably. The Y-piece 17 connects the two device-side flexible tubing 21.1 and 21.2 to the connector 25 and hence indirectly also to the connector 10.

The two flexible tubing 21.1 and 21.2, the connectors 10 and 25 as well as the Y-piece 17 belong to the device-side fluid guiding unit of the exemplary embodiment. This device-side fluid guiding unit 10, 17, 21.1, 21.2, 25 as well as the connection unit 20 form together a fluid guiding component. The fluid guiding component 10, 17, 20, 21.1, 21.2, 25 and the patient-side fluid guiding unit 11 form together a fluid guiding device. The fluid guiding device 10, 11, 17, 20, 21.1, 21.2, 25 and the patient-side coupling unit 19 form together a fluid guiding system.

Instead of a ventilation tube or measuring tube 19 in the body of the patient P, a breathing mask on the face of the patient P may also belong to the fluid guiding system 100. It is possible that the patient-side connection piece 2 of the connection unit 20 is connected directly to a connector of this breathing mask.

The fluid guiding units 10, 11, 17, 21.1, 21.2 and 25 are capable of guiding a fluid, especially breathing air or an anesthetic gas. The ventilator 30 causes the fluid to flow to the patient P. A volume flow sensor (flow sensor), not shown, measures the volume flow in the fluid guiding system 100, i.e., the volume flowing per unit of time. The values from the volume flow sensor are used, e.g., automatically to derive a parameter for the spontaneous breathing activity (spontaneous breathing) of the patient P, which parameter is variable over time, and to use this parameter for an automatic regulation of the ventilator 30 or to regulate the addition of an anesthetic.

The connection unit 20 according to the present invention allows the two connected fluid guiding units (connectors) 10 and 11 to have a plurality of degrees of freedom during the possible relative movements. The connector 11 can rotate about its own longitudinal axis relative to the connection unit 20. The connector 10 can likewise rotate about its own longitudinal axis relative to the connection unit 20. How this rotatable connection is embodied about two longitudinal axis, which are oriented obliquely in relation to one another, will be described below. In addition, the two flexible tubing 21.1 and 21.2 can rotate in the connection elements 22.1 and 22.2 about their longitudinal axes relative to the ventilator 30.

Thanks, in particular, to these properties of the connections, the flexible tubing 21.1, 21.2 and the connectors 25, 10, 11 of the fluid guiding system 100 are kept largely free from mechanical stresses and bending and twisting at the ventilator 30.

Figure 2:
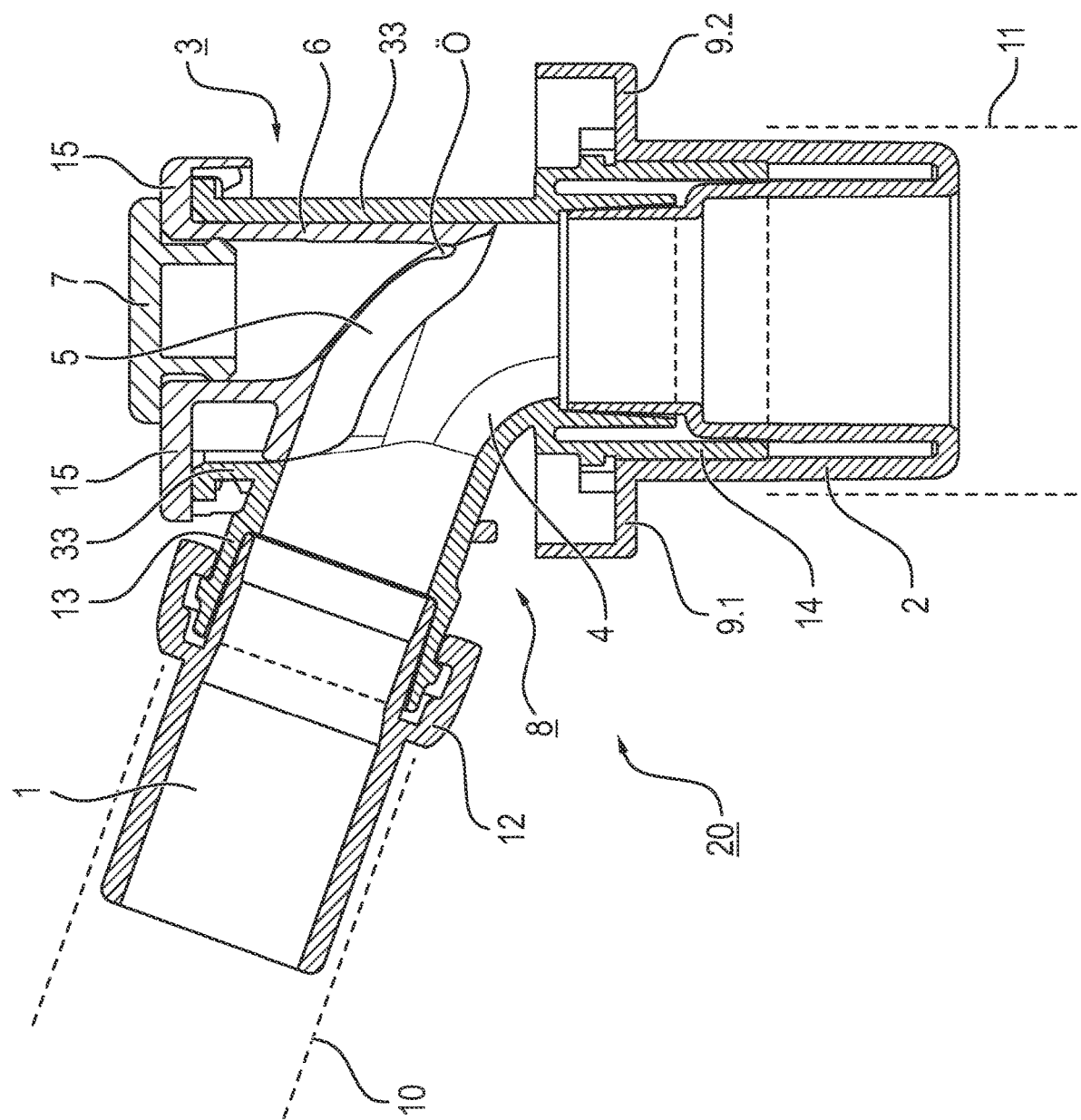
FIG. 2 is a cross-sectional view showing a connection unit.
Figure 3:
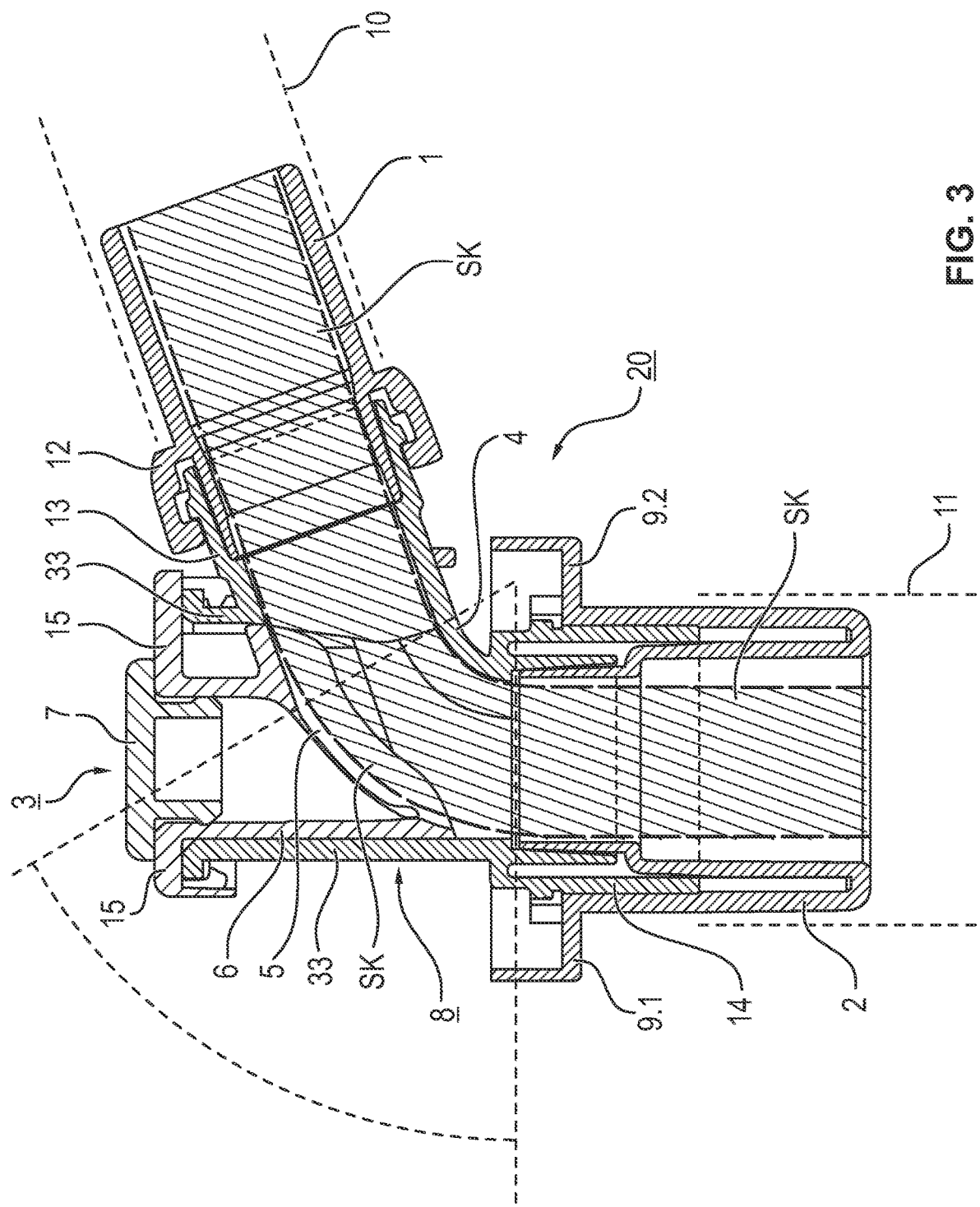
FIG. 3 is a cross-sectional view showing the connection unit.
Figure 4:
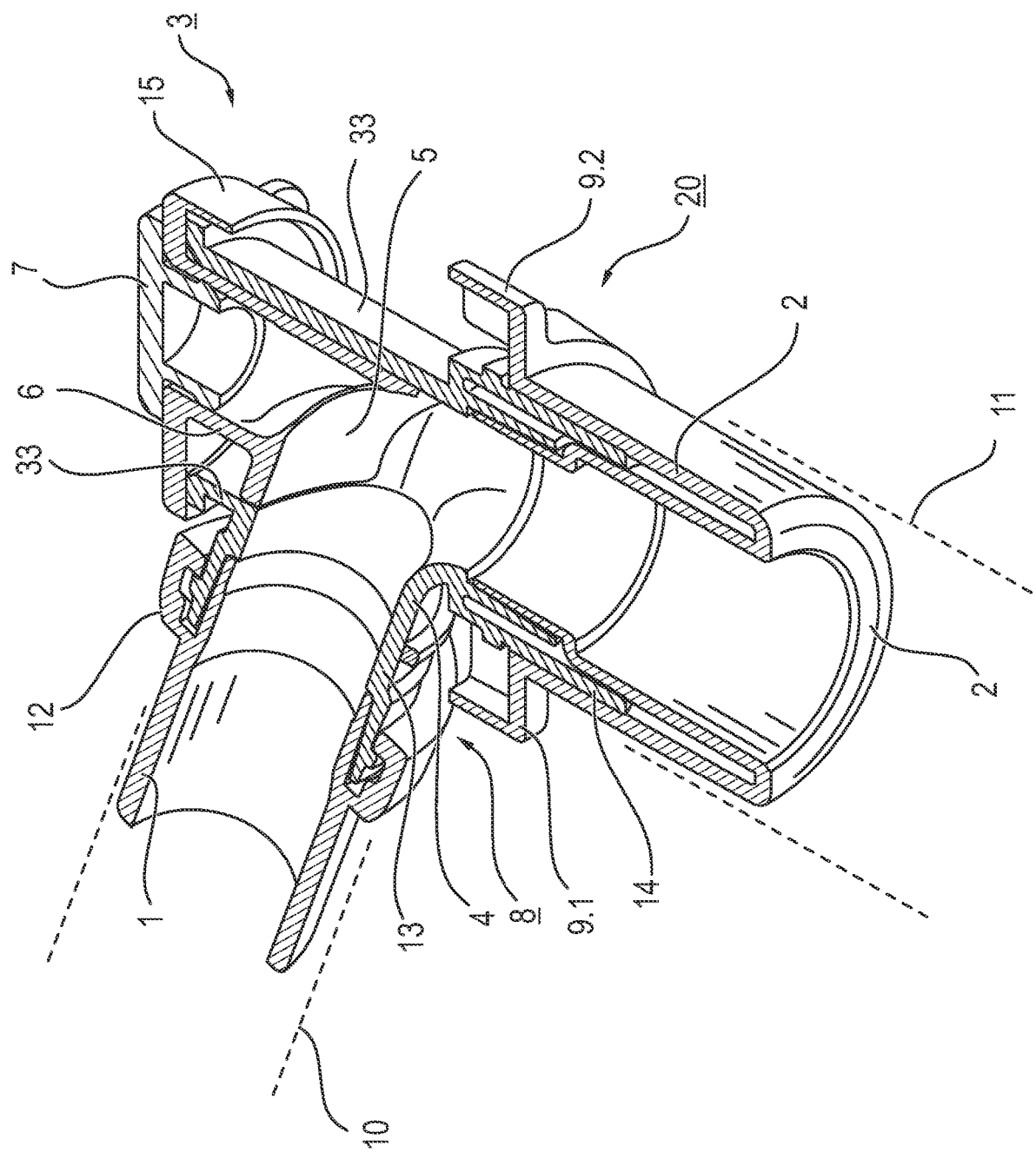
FIG. 4 is a perspective cross-sectional view showing the connection unit.
Figure 5:
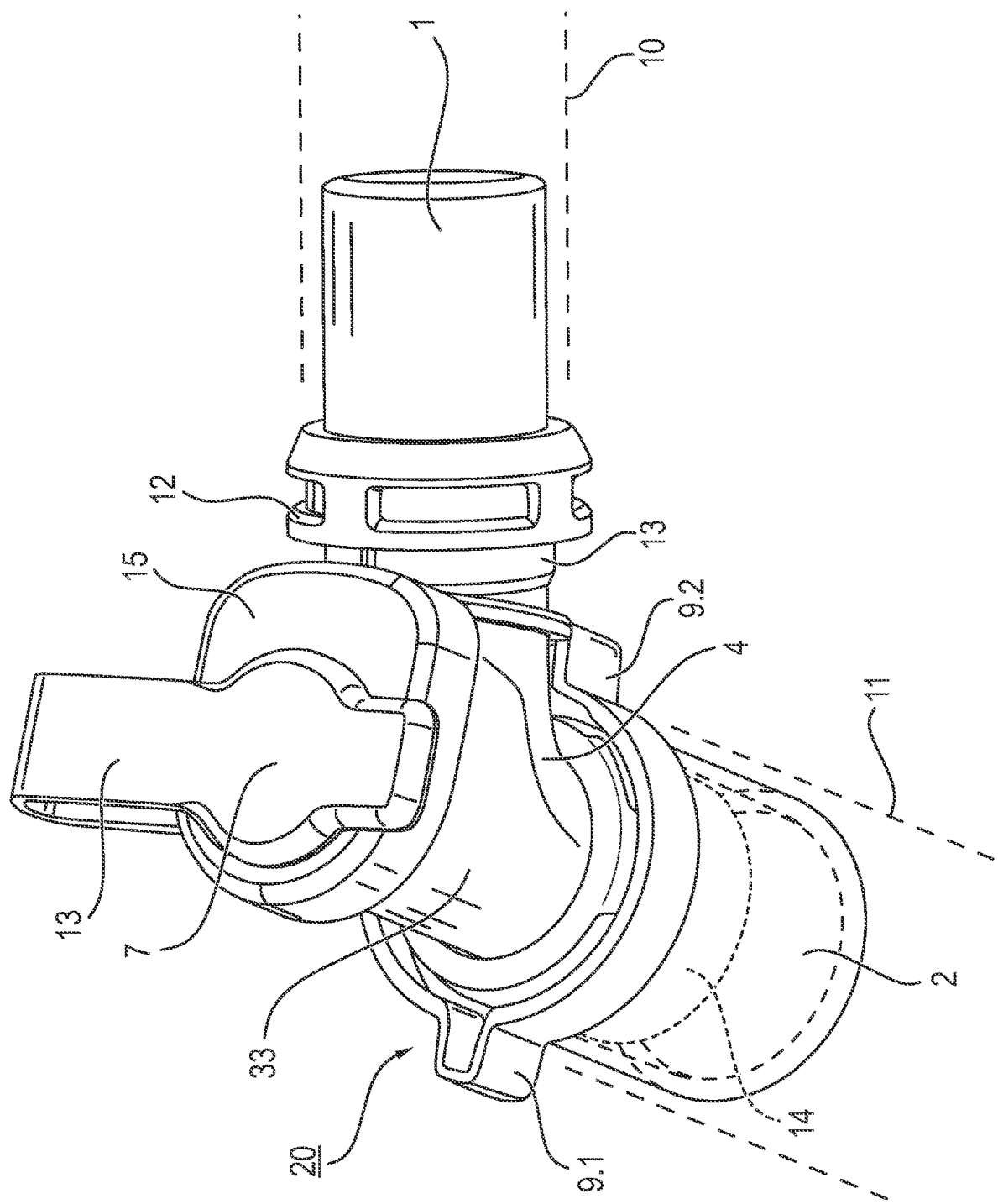
FIG. 5 is a perspective view showing the connection unit.
Figure 6:
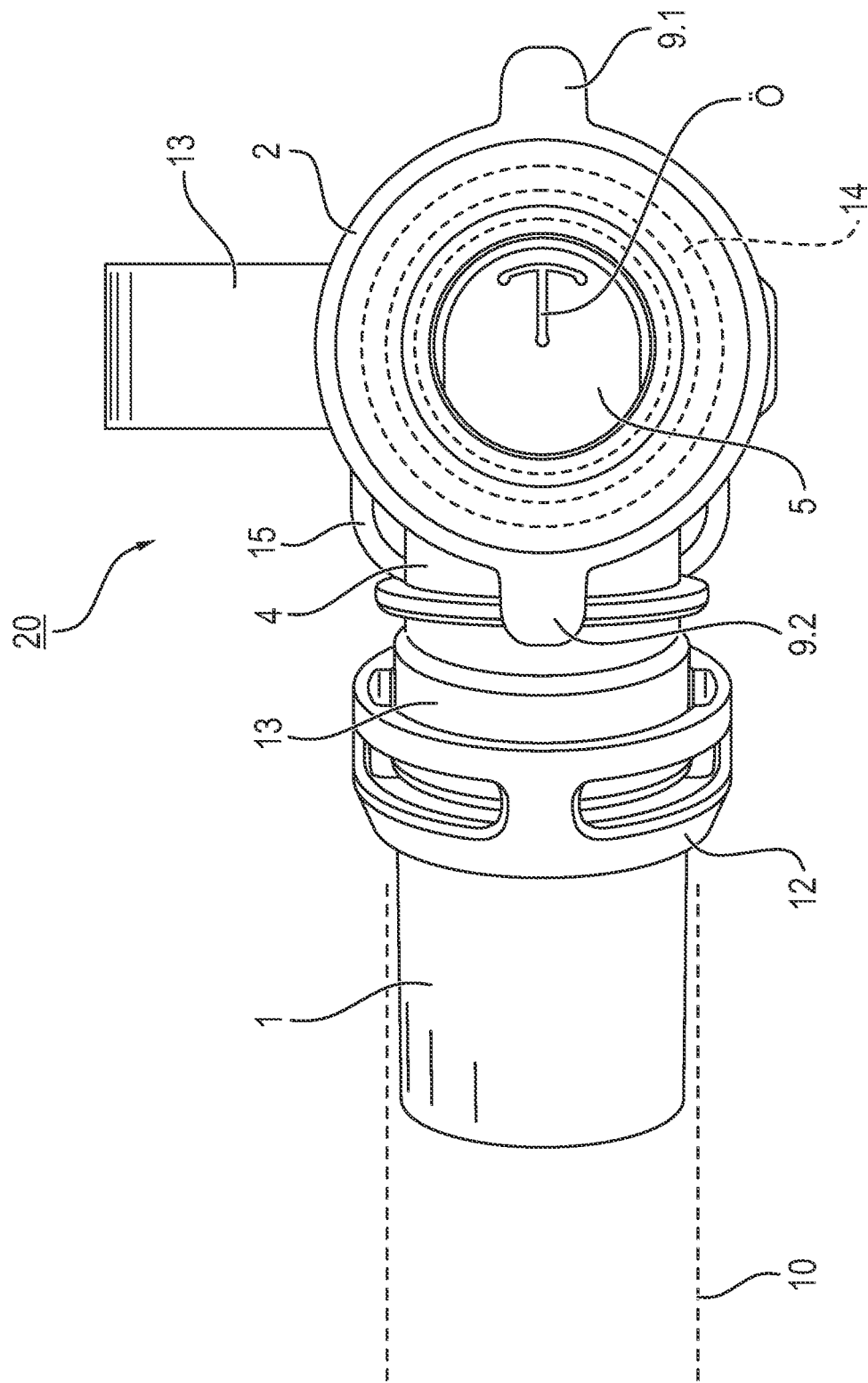
FIG. 6 is view from a direction parallel to the patient-side fluid guiding unit showing the connection unit.

FIG. 2 and FIG. 3 show the connection unit 20 according to the present invention in two cross-sectional views; FIG. 4 and FIG. 5 show it in two different perspective views, and FIG. 6 shows it in a viewing direction parallel to the patient-side fluid guiding unit (connector) 11. In addition, the patient-side fluid guiding unit (connector 11) and the device-side fluid guiding unit (connector 10) are suggested by broken lines.

The connection unit 20 according to the exemplary embodiment comprises the following components:
- a central piece (body) 8,
- a device-side connection piece 1,
- a patient-side connection piece 2 and
- a port piece 3.

The central piece 8 comprises
- a device-side straight tube segment 13,
- a curved tube segment 4,
- a straight connector 33 and
- a patient-side straight tube segment 14.

The three tube segments 13, 4 and 14 as well as the connector 33 are connected to one another rigidly and in a fluid-tight manner and pass continuously over one into the other. In particular, two adjacent tube segments 13 and 4 as well as 4 and 14 do not adjoin each other in an inner edge. An edge may be formed between the device-side straight tube segment 13 and the connector 33.

The two connection pieces 1 and 2, the three tube segments 13, 4 and 14 as well as a bent surface of a bent surface element 5, which bent surface will be described below, provide together a partially straight and partially bent tube (flow duct (flow passage) SK), wherein a fluid can flow through the flow passage SK in both directions and wherein the flow passage SK in the exemplary embodiment has the same cross-sectional area for fluid throughout. It is also possible that the flow passage SK narrows in one flow direction.

The direction of this flow passage SK changes continuously in the curved tube segment 4. The bent central piece 8 deflects a fluid stream, which flows through the flow passage SK, by an angle that is preferably between 35° and 90°, especially preferably between 50° and 80°, and especially between 60° and 70°. The duct, which is provided by the connector 33 and is preferably straight, opens into this flow passage SK.

The feature that the flow passage SK changes its direction in the curved tube segment 4 continuously preferably occurs in each position of a connection piece 1 or 2 relative to the central piece 8, i.e., independently from the rotation position of a connection piece 1 or 2. This feature of the continuous change in direction diminishes the risk of occurrence of swirls in the curved part of the flow passage SK. This feature is achieved especially by the inner walls of the three tube segments 13, 4 and 14 as well as the bent surface of the bent surface element 5 having no edges, not even at a transition. The flow passage SK provided therefore likewise has no edges. Another effect, which is achieved by the intentional absence of edges, is the following: The flow through the flow passage SK varies less over the position and/or over time, and the values that are provided by the volume flow sensor, not shown, have a narrower scatter and are more reliable than in the presence of an edge.

The device-side connection piece 1 is connected rotatably and in a fluid-tight manner to the device-side straight tube segment 13 of the central piece 8 and comprises a cone 12. The patient-side connection piece 2 is connected to the patient-side straight tube segment 14 of the central piece 8 rotatably and in a fluid-tight manner and comprises two grip elements 9.1 and 9.2 in one embodiment. It is also possible to provide only one grip element or more than two grip elements 9.1 and 9.2 or no grip elements at all. The two connection pieces 1 and 2 enclose each a part of a straight tube segment 13 and 14, respectively.

The patient-side fluid guiding unit, the connector 11 for the ventilation tube or for the measuring tube 19 or for a breathing mask of the fluid guiding system 100 in the exemplary embodiment, can be connected to the patient-side connection piece 2 in a fluid-tight manner and rotating in unison. The connector 11 is preferably enclosed by the patient-side connection piece 2, i.e., a device-side end of the connector 11 is located within the patient-side connection piece 2. If a breathing mask is used as the patient-side fluid guiding unit, the connector thereof preferably encloses the patient-side connection piece 2. The patient-side connection piece 2 is preferably configured as an M22/F15 double cone according to ISO 5356-1, which has a pitch of 1:40.

The device-side fluid guiding unit, the connector 10 in the exemplary embodiment, can be connected to the device-side connection piece 1 in a fluid-tight manner and rotating in unison. The patient-side end of the connector 10 preferably encloses the device-side connection piece 1. The device-side connection piece 1 is preferably configured as an M15 cone according to ISO 5356-1.

The curved tube segment 4 of the central piece 8 has a receiving opening in its wall, which is an outer wall when viewed in the direction of the curvature. The end of the straight connector 33, which end points towards the central piece 8, encloses this receiving opening.

Figure 7:
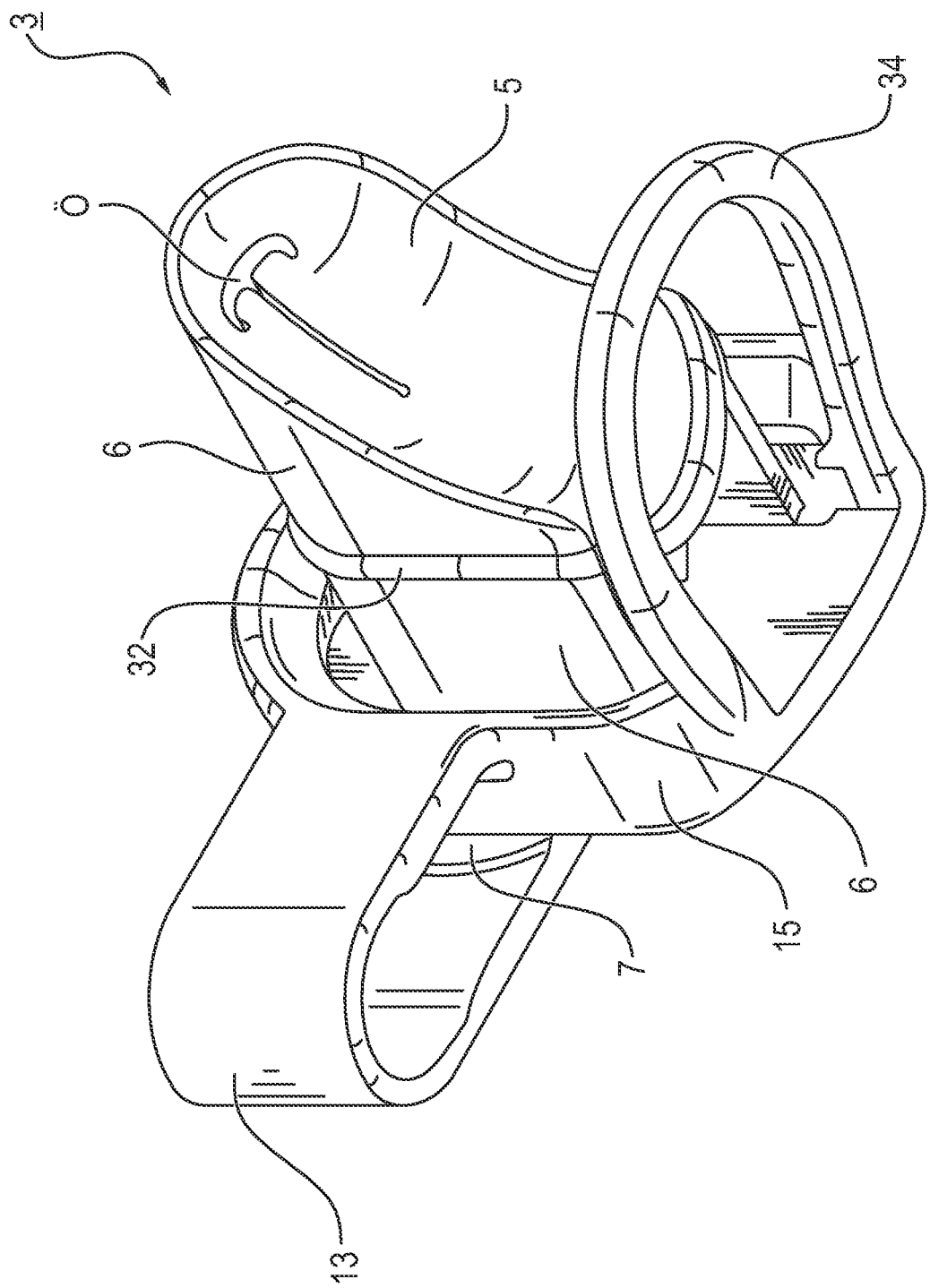
FIG. 7 is a perspective view of a port piece.
Figure 8:
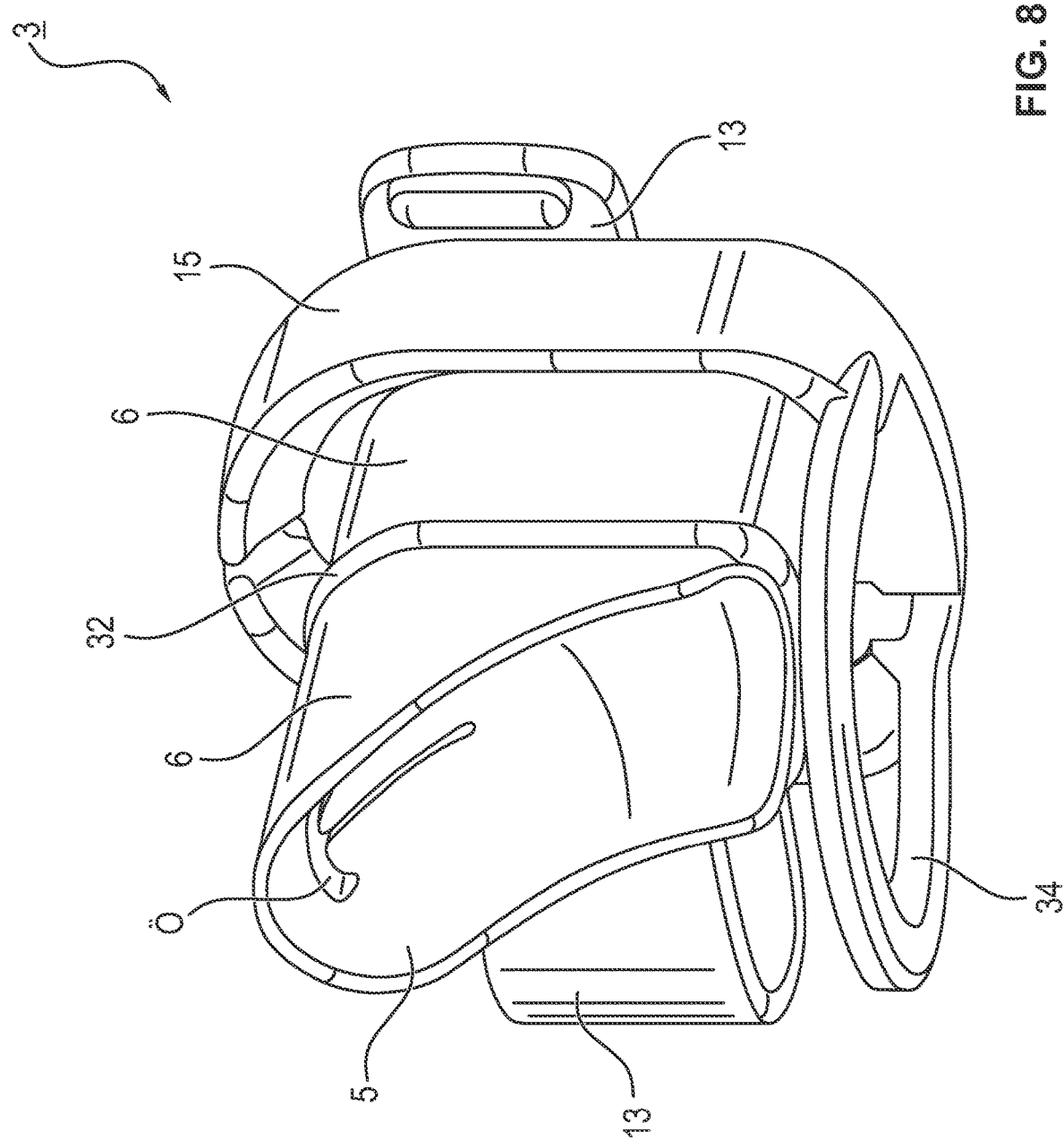
FIG. 8 is another perspective view of the port piece.

FIG. 7 and FIG. 8 show the port piece 3 in two perspective views from two different viewing directions. The port piece 3 comprises
- a straight tube segment 6 with a circumferential projection 32,
- a flange 15 at the end of the straight tube segment 6, which end is located at a distance from the central piece 8,
- a bent surface element 5 with a bent surface 5 at the other end of the straight tube segment 6, wherein a receiving opening Ö is recessed into the bent surface element,
- an optional strap 34 for holding the port piece 3,
- an optional cap 7, and
- an optional holder 13 for the cap 7.

The cap 7 can be inserted into an opening in the flange 15 and can be removed again. The cap 7 is inserted in FIG. 7 and in FIG. 8. The inserted cap 7 closes the flange 15. The holder 13 holds the cap 7 at the flange 15 and prevents the cap 7 from falling off all by itself, e.g., because of vibrations or when it is not attached. The attached cap 7 prevents fluid or particles from flowing from the outside through the straight tube segment 6 and into the flow passage SK or conversely, it prevents fluid from being discharged from the flow passage SK through the straight tube segment 6 to the outside. The port piece 3 can be grasped by the strap.

The entire port piece 3 can preferably be inserted into the straight connector 33. The bent surface element 5 then fills the receiving opening, aside from the passage opening Ö described below, completely and in a fluid-tight manner. The straight tube segment 6 connects this receiving opening to the flange 15. The straight connector 33 of the central piece 8 encloses the straight tube segment 6 of the port piece 3. This configuration makes it possible to manufacture the port piece 3 separately from the rest of the connection unit 20, and it makes it, furthermore, easier to manufacture the port piece 3 from a material different from the material of the rest of the connection unit 20. The inner profile of the straight connector 33 is preferably identical to the outer profile of the straight tube segment 6. The two profiles are preferably configured such that the port piece 3 can be inserted in a defined position only relative to the straight connector 33, aside from an optional circumferential gap. The bent surface of the bent surface element 5 closes flush with the inner wall of the central piece 8.

In one embodiment, the port piece 3 is connected to the central piece 8 by a joint connection in a fluid-tight manner, for example, by a bonded connection or a by a welded connection. When manufacturing the connection unit 20, the port piece 3 is inserted into the central piece 8 and is connected to this. Thanks to this joint connection, the port piece 3 cannot be pulled out of the central piece 8 without destruction any longer.

In another embodiment, the port piece 3 can be pulled out of the central piece 8 again without destruction. A snap holder or another snap-in unit preferably holds the port piece 3 in the central piece in a positive-locking manner.

The entire port piece 3 is preferably manufactured from an elastic, i.e., reversibly deformable material, preferably in one piece or even monolithically (manufactured in a single step). More precisely, the elasticity of the port piece 3 is greater than the elasticity of the central piece 8 and than the elasticity of the connection pieces 1 and 2. The higher elasticity of the port piece 3 reduces the risk of development of a leak between the inserted port piece 3 and the central piece 8. It is possible that the port piece 3 is slightly compressed during insertion into the straight connector 33 of the central piece 8 and it is reversibly deformed thereby and the deformed bent surface element 5 with the bent surface 5 nestles up and thereby adapts itself to the edge of the receiving opening based on the intrinsic restoring force.

It is also possible that a circumferential gap develops between the straight connector 33 and the straight tube segment 6 of the port piece 3. This gap makes it easier to insert the port piece 3 into the connector 33. The circumferential projection 32 pushes against the straight connector 33 from the inside, closes this gap and further reduces the risk of a leak. In one embodiment, the straight tube segment 6 snaps into the connector 33.

The straight tube segment 6 of the connection piece 3, the patient-side straight tube segment 14 and the patient-side connection piece 2 together provide a straight, continuous tube, which opens precisely into the patient-side fluid guiding unit 11 and is interrupted and largely closed by the bent surface element 5. The bent surface element 5 occupies according to the present invention at least half, preferably at least 80%, especially preferably at least 90% or even at least 95% of the receiving opening when no additional device is inserted. The rest of the receiving opening is occupied by the passage opening Ö. The passage opening Ö preferably occupies at least 20% of the receiving opening.

An intracorporeal device, for example, a suction catheter or an endoscope or a sensor, can be inserted through this straight tube into the patient-side fluid guiding unit 11 from the outside, without the fluid connection between the patient P and the ventilator 30 having to be broken. A rod-shaped intracorporeal device 40 is shown schematically in FIG. 1, and the insertion direction is indicated by an arrow. For example, secretions can be aspirated from the patient by means of this intracorporeal device 40, or the patient P or the fluid stream can be examined. For example, a measuring probe can be brought into the proximity of the lungs of the patient P. The preferably rigid patient-side fluid guiding unit 11 can be used to guide the intracorporeal device 40 to the patient P, and it surrounds the intracorporeal device 40. The ventilator 30 is capable of ventilating the patient P mechanically even while the intracorporeal device 40 is being inserted and is subsequently being used. It is also possible to introduce medication, contrast media or other substances into the body of the patient P through the straight tube.

As was mentioned already, the port piece 3 can preferably be inserted into the receiving opening. The port piece 3 can be manufactured separately from the rest of the connection unit 20. This embodiment makes it possible to manufacture and to use different connection units for different purposes. The different connection units preferably differ exclusively by different port pieces 3, for example, connectors 33 of different sizes, while the connection units otherwise have the same configuration. This embodiment reduces the variance and makes it possible to manufacture the rest of the connection unit 20 in a larger quantity and to manufacture only the port piece 3 in different variants for the different applications and in smaller quantities per variant.

To insert the intracorporeal device 40 into the connection unit 20, it is necessary first to remove the cap 7 from the flange 15. It is, however, not necessary for the insertion, thanks to the straight tube 6, 14, 2, to detach the connection unit 20 from the ventilator 30 or to sever the connection between the connection unit 20 and the patient-side fluid guiding unit 11.

If the entire port piece 3 were pulled out of the central piece 8 in order to insert the intracorporeal device 40 with the mechanical ventilation going on, the entire receiving opening would be opened. The risk that the ventilator 30 is unable to maintain a sufficiently high pneumatic end-expiratory pressure (PEEP) in the lungs of the patient P is high. The port piece 3 is configured therefore such that the intracorporeal device 40 can be inserted with the port piece 3 inserted.

If the intracorporeal device 40 shall be inserted with the port piece 3 inserted, the bent surface element 5 must be penetrated. The passage opening Ö is therefore penetrated through the bent surface element 5. The device 40 punctures this passage opening Ö during the insertion. This is possible because of the elasticity of the bent surface element 5, without damaging the bent surface element 5, even if the intracorporeal device 40 is broader than the passage opening Ö. As long as no intracorporeal device is inserted, the passage opening Ö occupies only a small area of the bent surface, preferably at most 20%, especially at most 10% or even at most 5%, because of the elasticity of the bent surface element 5. As a result, only a relatively small quantity of fluid escapes to the outside from the flow passage SK through the straight tube segment 6 or, conversely, enters into the flow passage SK from the outside, even when no intracorporeal device is inserted. In other words, only small losses occur due to leakage. The ventilator 30 can therefore maintain a sufficient end-expiratory pressure (PEEP) in the lungs of the patient P.

It is not necessary in many cases to adapt the geometry of the passage opening Ö to the geometry of an intracorporeal device 40 to be inserted. Different intracorporeal devices 40 with different geometries can be inserted and removed again one after another through the same passage opening Ö. Since the passage opening Ö causes only a small hole in the wall of the flow passage SK when no device 40 is inserted, it is unnecessary in many cases to insert the intracorporeal device 40 very rapidly after removal of the cap 7 in order to largely reclose the flow passage SK.

It is possible that the passage opening Ö is enclosed by sealing lips or other deformable elements, which have a greater elasticity and/or deformability than the rest of the bent surface element 5. For example, the sealing lips are manufactured from rubber, while the rest of the port piece 3 is manufactured from a harder plastic. Or else, the entire port piece 3 is manufactured from a sufficiently flexible material, e.g., rubber. The intracorporeal device 40 to be inserted can therefore have a larger dimension in a direction at right angles to the longitudinal axis of the straight tube made available than the passage opening Ö when no intracorporeal device 40 is inserted.

The passage opening Ö preferably has an elongated configuration and extends along a longitudinal axis; in particular, the maximum dimension is at least twice the dimension at right angles to the longitudinal axis. As a result, the passage opening Ö can be opened especially wide in order to insert the device 40. In one embodiment, the passage opening Ö has the shape of a slot. It is also possible that the opening Ö has the shape of a common anchor, cf. FIG. 6, or the shape of a star or of an ellipse or of a semicircle. In conjunction with the elasticity of the bent surface element 5, this configuration makes it easier to insert an intracorporeal device 40 with a relatively large cross-sectional area through the passage opening Ö, while the area of the passage opening Ö is at the same time small when no intracorporeal device 40 is inserted.

In a preferred embodiment, the central piece 8, the two connection pieces 1 and 2 as well as the port piece 3 are manufactured separately from one another. The port piece 3 is inserted into the central piece 8. The bent surface element 5 of the port piece 3 is inserted here into the receiving opening in the central piece 8, so that the bent surface adjoins flush with the inner wall of the central piece 8. The connection pieces 1 and 2 are placed subsequently or before on the two ends of the central piece 8, so that a rotatable fluid-tight connection is established.

At least the central piece 8 and the two connection pieces 1 and 2, and optionally also the port piece 3 are preferably manufactured by an injection molding process. It is also possible that the port piece 3 is manufactured by casting, for example, from rubber, preferably as a single component, by means of a corresponding casting mold or of a respective casting mold per variant of the port piece 3. As was already described above, the receiving opening in the central piece 8, into which receiving opening the port piece 3 is later inserted, extends in the flow direction over the entire extension of the outer wall. This embodiment avoids undercuts in the central piece 8 and makes it easier to provide and to use a two-part mold for the injection molding. In one embodiment, one half of a bent tube is manufactured and is connected to the two straight tube segments 13 and 14 permanently and in a fluid-tight manner.

While specific embodiments of the invention have been shown and described in detail to illustrate the application of the principles of the invention, it will be understood that the invention may be embodied otherwise without departing from such principles.

LIST OF REFERENCE CHARACTERS

1 Device-side connection piece; it is connected to the device-side tube segment 13 rotatably and in a fluid-tight manner; it can be connected by means of the cone 12 to the device-side fluid guiding unit 10 such that they rotate in unison

2 Patient-side connection piece; it is connected to the patient-side tube segment 14 rotatably and in a fluid-tight manner; it can be connected to the patient-side fluid guiding unit 11 such that they rotate in unison

3 Port piece for connecting an intracorporeal device 40 or for introducing drugs; it is inserted into a receiving opening in the central piece 8

4 Curved tube segment of the central piece 8; it is connected to the two straight tube segments 13 and 14 permanently and in a fluid-tight manner; it has a receiving opening for receiving the port piece 3

5 Bent surface element of the port piece 3; the bent surface element has the bent surface and the receiving opening Ö; the bent surface element fills out the receiving opening

6 Straight tube segment of the port piece 3; it leads from the flange 15 to the bent surface element 5; it can be closed by the cap 7

7 Cap for closing the straight tube segment 6; it can be placed on the flange 15

8 Central piece; it comprises the straight tube segments 13 and 14 as well as the curved tube segment 4; it is connected rotatably to the two connection pieces 1 and 2 and permanently to the connector 33; it has a receiving opening, with which the port piece 3 meshes

9.1, 9.2 Opposite grip elements at the patient-side connection piece 2

10 Device-side fluid guiding unit in the form of a tubular connector; it is connected to the device-side connection piece 1 in a fluid-tight manner

11 Patient-side fluid guiding unit in the form of a tubular connector between the patient-side connection piece 2 and the ventilation tube 19; the patient-side fluid guiding unit is connected to the patient-side connection piece 2 in a fluid-tight manner

12 Cone at the device-side connection piece 1; it encloses the device-side straight tube segment 13

13 Device-side straight tube segment of the central piece 8; it is connected rotatably to the device-side connection piece 1

14 Patient-side straight tube segment of the central piece; it is connected rotatably to the patient-side connection piece 2; it comprises the two grip elements 9.1 and 9.2

15 Flange of the connection piece 3; it adjoins the straight tube segment 6; it has an opening, which can be closed by the cap 7

17 Y-piece; it connects the two device-side flexible tubing 21.1 and 21.2 to the connector 25

19 Patient-side coupling unit in the form of a measuring tube; which reaches the stomach of the patient P, or in the form of a ventilation tube, which is inserted into the trachea of the patient P; it is connected to the connector 11 in a fluid-tight manner

20 Connection unit according to the present invention; it comprises the device-side connection piece 1, the patient-side connection piece 2, the port piece 3 and the central piece 8; it is connected to the two fluid guiding units (connectors) 10 and 11 in a fluid-tight manner

21.1,

21.2 Device-side flexible tubing for the inhalation and for the exhalation; connected to the connection elements 22.1 and 22.2, respectively

22.1,

22.2 Connection elements for a rotatable connection between the device-side flexible tubing 21.1 and 21.2 and the ventilator 30

24 Filter against microbes and viruses; arranged between the two connectors 10 and 25

25 Fluid guiding unit in the form of a connector; it connects the Y-piece 17 to the filter 24

30 Ventilator; it comprises the display device 31; it is connected to the fluid guiding system 100 via the two connection elements 22.1, 22.2

31 Display device of the ventilator 30; it makes possible the display of vital parameters of the patient P while the ventilator 30 is connected to the patient P via the fluid guiding system 100

32 Circumferential projection on the straight tube segment 6

33 Straight connector for receiving the port piece 3; it belongs to the central piece 8; it is permanently connected to the curved tube segment 4; it ends in the receiving opening

34 Strap for holding the port piece 3 at the central piece 8

40 Intracorporeal device, which can be inserted through the port piece 3 and the patient-side fluid guiding system 11

100 Fluid guiding system; the fluid guiding system comprises the ventilation tube 19, the central piece 8, the two device-side flexible tubing 21.1 and 21.2, the two device-side connectors 10 and 25, the Y-piece 17 and the connection unit 20 according to the present invention; it is connected rotatably to the ventilator 30 via the two connection elements 22.1 and 22.2

Ö Passage opening in the bent surface 5 for passing through an intracorporeal device 40

P Patient, who is mechanically ventilated; he is connected to the ventilator 30 via the fluid guiding system 100

SK Partially curved flow passage; it passes through the connection unit 20; it is provided by the inner walls of the central piece 8 and the connection pieces 1 and 2

What is claimed is:

1. A connection unit for establishing a fluid connection between a patient-side coupling unit and a medical device, the connection unit comprising:
    a hollow patient-side connection piece for connecting a patient-side fluid guiding unit, which is connectable to the patient-side coupling unit;
    a hollow device-side connection piece for connecting a device-side fluid guiding unit, which is connectable to the medical device;
    a port piece comprising a straight tube segment and a bent surface element with a bent surface and with a passage opening, wherein the passage opening is arranged in the bent surface of the bent surface element and occupies at most half of the bent surface of the bent surface element; and
    a hollow central piece with two ends, wherein the central piece comprises a curved tube segment with a wall, wherein one end of the central piece is fluid-tight connected to the patient-side connection piece and another end of the central piece is fluid-tight connected to the device-side connection piece, wherein:
the hollow patient-side connection piece, the hollow device-side connection piece, and the curved tube segment provide a curved flow passage;
the port piece is insertable into a receiving opening of the central piece such that the bent surface of the bent surface element forms a part of the wall of the curved tube segment; and
the straight tube segment of the port piece and the central piece together provide a straight flow passage, which is interrupted by the bent surface element of the inserted port piece and passes through the passage opening and continues in an interior of the patient-side connection piece.

2. A connection unit in accordance with claim 1, wherein the port piece is detachably connected to the central piece.

3. A connection unit in accordance with claim 1, wherein: the port piece is made of a material that has a greater elasticity than material of the central piece.

4. A connection unit in accordance with claim 1, wherein the connection unit comprises a cap with which the straight tube segment can be reversibly closed.

5. A connection unit in accordance with claim 1, wherein the bent surface element with the bent surface provides at least two mutually opposite sealing lips or a circumferential sealing lip, which define or defines the passage opening.

6. A connection unit in accordance with claim 1, wherein the curved flow passage is configured such that a direction of a fluid flowing through the curved flow passage is deflected by an angle that is between 35° and 90°.

7. A connection unit in accordance with claim 1, wherein:
the wall of the curved tube segment has, in relation to a direction of curvature, a bent inner wall segment and a bent outer wall segment; and
the bent surface of the bent surface element forms an entirety of the bent outer wall segment or a part of the bent outer wall segment; and
the bent surface of the bent surface element comprises at least 50% of the surface of the bent outer wall segment.

8. A connection unit in accordance with claim 1, wherein:
the central piece comprises a connector, which encloses the receiving opening of the central piece;
the port piece is insertable into the connector; and
the port piece is snappable, so as to be snapped in the connector.

9. A fluid guiding system comprising a fluid guiding component comprising:
a device-side fluid guiding unit; and
a connection unit, the connection unit comprising:
a hollow patient-side connection piece for connecting a patient-side fluid guiding unit, which is connectable to a patient-side coupling unit;
a hollow device-side connection piece for connecting the device-side fluid guiding unit, which is connectable to a medical device;
a port piece comprising a straight tube segment and a bent surface element with a bent surface and with a passage opening, wherein the passage opening is arranged in the bent surface of the bent surface element and occupies at most half of the bent surface of the bent surface element; and
a hollow central piece with two ends, wherein the central piece comprises a curved tube segment with a wall, wherein one end of the central piece is fluid-tight connected to the patient-side connection piece and another end of the central piece is fluid-tight connected to the device-side connection piece, wherein:
the hollow patient-side connection piece hollow device-side connection piece and the curved tube segment provide a curved flow passage;
the port piece is insertable into a receiving opening of the central piece such that the bent surface of the bent surface element forms a part of the wall of the curved tube segment;
the straight tube segment of the port piece and the central piece together provide a straight flow passage, which is interrupted by the bent surface element of the inserted port piece, passes through the passage opening and continues in an interior of the patient-side connection piece;
the device-side connection piece of the connection unit is configured to be fluid-tight connectable to the device-side fluid guiding unit; and
the device-side fluid guiding unit is configured to be fluid-tight connectable to the medical device.

10. A fluid system according to claim 9, further comprising a patient-side fluid guiding unit, wherein:
the patient-side connection piece of the connection unit is configured to be fluid-tight connectable to the patient-side fluid guiding unit; and
the patient-side fluid guiding unit is configured to be fluid-tight connectable to the patient-side coupling unit.

11. A fluid guiding system according to claim 10, further comprising a medical device, wherein the connection unit provides a fluid connection between the patient-side coupling unit and the medical device.

12. A fluid guiding system according to claim 11, wherein the medical device is a ventilator configured to ventilate a patient.

13. A fluid guiding system in accordance with claim 11, wherein the port piece is detachably connected to the central piece.

14. A fluid guiding system in accordance with claim 13, wherein:
the central piece comprises a connector, which encloses the receiving opening of the central piece;
the port piece is insertable into the connector; and
the port piece is snappable, so as to be snapped in the connector.

15. A fluid guiding system in accordance with claim 11, wherein:
the port piece is made of a material that has a greater elasticity than material of the central piece.

16. A fluid guiding system in accordance with claim 11, wherein the connection unit comprises a cap with which the straight tube segment can be reversibly closed.

17. A fluid guiding system in accordance with claim 11, wherein the bent surface element with the bent surface provides at least two mutually opposite sealing lips or a circumferential sealing lip, which define or defines the passage opening.

18. A fluid guiding system in accordance with claim 11, wherein the curved flow passage is configured such that a direction of a fluid flowing through the curved flow passage is deflected by an angle that is between 35° and 90°.

19. A fluid guiding system in accordance with claim 11, wherein:
the wall of the curved tube segment has, in relation to a direction of curvature, a bent inner wall segment and a bent outer wall segment;

the bent surface of the bent surface element forms an entirety of the bent outer wall segment or a part of the bent outer wall segment; and the bent surface of the bent surface element comprises at least 50% of the surface of the bent outer wall segment.

20. A connection unit process for a connection unit comprising: a hollow patient-side connection piece for connecting a patient-side fluid guiding unit, which is connectable to a patient-side coupling unit; a hollow device-side connection piece for connecting a device-side fluid guiding unit, which is connectable to a medical device; a port piece comprising a straight tube segment and a bent surface element with a bent surface and with a passage opening, wherein the passage opening is arranged in the bent surface of the bent surface element and occupies at most half of the bent surface of the bent surface element; and a hollow central piece with two ends, wherein the central piece comprises a curved tube segment with a wall, wherein one end of the central piece is fluid-tight connected to the patient-side connection piece and another end of the central piece is fluid-tight connected to the device-side connection piece, wherein: the hollow patient-side connection piece hollow device-side connection piece and the curved tube segment provide a curved flow passage; the port piece is insertable into a receiving opening of the central piece such that the bent surface of the bent surface element forms a part of the wall of the curved tube segment; and the straight tube segment of the port piece and the central piece together provide a straight flow passage, which is interrupted by the bent surface element of the inserted port piece, passes through the passage opening and continues in an interior of the patient-side connection piece, the process comprising the steps of:

manufacturing the port piece;

manufacturing the hollow patient-side connection piece;

manufacturing the hollow device-side connection piece;

manufacturing the central piece such that the wall of the central piece has the receiving opening;

inserting the port piece into the receiving opening such that the bent surface element of the port piece closes the receiving opening; and fluid-tight connecting the central piece to the hollow patient-side connection piece and fluid-tight connecting the central piece the hollow device-side connection piece.

21. A connection unit process in accordance with claim 19, further comprising establishing a fluid connection between the patient-side coupling unit and the medical device with the connection unit.

* * * * *